(12) United States Patent
Bellini et al.

(10) Patent No.: US 8,575,129 B2
(45) Date of Patent: *Nov. 5, 2013

(54) AMIDES OF HYALURONIC ACID AND THE DERIVATIVES THEREOF AND A PROCESS FOR THEIR PREPARATION

(75) Inventors: Davide Bellini, Montegrotto Terme (IT); Alessandra Topai, Rome (IT)

(73) Assignee: Fidia Farmaceutici S.p.A., Abano Terme (IT)

( * ) Notice: Subject to any disclaimer, the term of this patent is extended or adjusted under 35 U.S.C. 154(b) by 325 days.

This patent is subject to a terminal disclaimer.

(21) Appl. No.: 12/623,253

(22) Filed: Nov. 20, 2009

(65) Prior Publication Data

US 2010/0158796 A1 Jun. 24, 2010

Related U.S. Application Data

(63) Continuation of application No. 10/220,853, filed as application No. PCT/IB99/01254 on Jul. 6, 1999.

(30) Foreign Application Priority Data

Jul. 6, 1998 (IT) .................................. PD98A0169

(51) Int. Cl.
*A61K 31/728* (2006.01)
*A61K 31/715* (2006.01)
*A61K 31/738* (2006.01)

(52) U.S. Cl.
USPC ........... 514/54; 536/123.1; 536/124; 424/443

(58) Field of Classification Search
USPC .................... 514/54; 536/123.1, 124; 424/443
See application file for complete search history.

(56) References Cited

U.S. PATENT DOCUMENTS

| 5,612,360 | A |   | 3/1997 | Boyd et al. |
| 5,644,049 | A |   | 7/1997 | Giusti et al. |
| 5,658,582 | A |   | 8/1997 | Dorigatti et al. |
| 5,733,891 | A | * | 3/1998 | Akima et al. ................... 514/59 |
| 6,110,967 | A |   | 8/2000 | Asao et al. |
| 6,579,978 | B1 |  | 6/2003 | Renier et al. |

FOREIGN PATENT DOCUMENTS

| EP | 0 216 453 | | 4/1987 |
| EP | 0 340 628 A2 | | 11/1989 |
| EP | 0 416 250 A2 | | 3/1991 |
| EP | 0 506 976 A1 | | 10/1992 |
| EP | 0 554 898 A2 | | 8/1993 |
| EP | 0 656 215 A1 | | 6/1995 |
| EP | 0 713 859 A2 | | 5/1996 |
| JP | 55161801 | | 12/1980 |
| JP | 3047801 | | 2/1991 |
| JP | 6-80666 A | | 12/1993 |
| JP | 9188705 | | 7/1997 |
| JP | 9296005 | | 11/1997 |
| JP | 10120705 | | 5/1998 |
| JP | 10-298164 A | | 11/1998 |
| WO | WO-89/02445 | | 3/1989 |
| WO | WO-92/06714 A1 | | 4/1992 |
| WO | WO-92/20349 | | 11/1992 |
| WO | WO-95/24429 | | 9/1995 |
| WO | WO 9524429 | * | 9/1995 |
| WO | WO-96/35721 | | 11/1996 |
| WO | WO-98/47887 A1 | | 10/1998 |
| WO | WO-98/54335 | | 10/1998 |

OTHER PUBLICATIONS

Aspinall et al. (Biochemistry (1994), 33(1), 250-5).*
Japanese Office Action issued in corresponding Japanese application No. 2006-254511 on Feb. 2, 2010.
Aspinall et al., Biochemistry, 1994, 33(1), pp. 250-255.
Danishefsky et al., Carbohydrate Research, vol. 16, pp. 199-205, 1971.

* cited by examiner

*Primary Examiner* — Shaojia Anna Jiang
*Assistant Examiner* — Michael C Henry
(74) *Attorney, Agent, or Firm* — Birch, Stewart, Kolasch & Birch, LLP

(57) ABSTRACT

An amide of hyaluronic acid or a derivative thereof which comprises at least one repetitive unit of general formula (I): wherein $R=NR_6R_7$, or alcoholic group of the aliphatic, aromatic, arylaliphatic, cycloaliphatic, heterocyclic series, OH, O—, alcoholic group of hyaluronic acid, amino group of deacylated hyaluronic acid; $R_1$, $R_2$, $R_3$, $R_4$=H, $SO_3$—, acyl group derived from a carboxylic acid of the aliphatic, aromatic, arylaliphatic, cycloaliphatic, heterocyclic series, —CO—$(CH_2)_2$—COOY; Y=negative charge, or H; $R_5$=—CO—$CH_3$, H, $SO_3$—, acyl group derived from a carboxylic acid of the aliphatic, aromatic, arylaliphatic, cycloaliphatic, heterocyclic series, acylic group of hyaluronic acid; $R_6$=is H or a aliphatic, aromatic, arylaliphatic, cycloaliphatic, or heterocyclic group, substituted or unsubstituted; $R_7$=is H or an aliphatic, aromatic, arylaliphatic, cycloaliphatic, or heterocyclic group, substituted or unsubstituted; wherein at least one of R or $R_5$ forms an amide group.

28 Claims, 3 Drawing Sheets

AMIDES OF HYALURONIC ACID AND THE DERIVATIVES THEREOF AND A PROCESS FOR THEIR PREPARATION

CROSS-REFERENCE

This application is a Continuation of pending U.S. application Ser. No. 10/220,853, filed on Sep. 6, 2002, which is the national stage application of PCT/IB99/01254, filed on Jul. 6, 1999, which designated the United States and which claims priority to Italian Application PD98A000169 filed on Jul. 6, 1998. The entire contents of the above applications are hereby incorporated by reference.

SUBJECT OF THE INVENTION

The present invention is directed to amides of hyaluronic acid and derivatives thereof for the preparation of pharmaceutical formulations, of biomaterials and for the coating of biomedical objects and the process for their preparation.

FIELD OF THE INVENTION

Hyaluronic acid is a heteropolysaccharide composed of alternate residues of D-glucuronic acid and N-acetyl-D-glycosamine. It is a straight-chained polymer the molecular weight of which varies between 50,000 and 13,000,000 Da depending on the source from which it was obtained and the methods used to obtain it. It is present in nature in pericellular gels, in the fundamental substance of the connective tissue of vertebrate organisms of which it represents one of the main components, in the synovial fluid of the joints, in the vitreous humor, in the human umbilical cord tissues and in rooster combs.

In recent years, numerous types of hyaluronic acid derivatives have been synthesized to obtain compounds with pharmacological properties, or compounds that can be processed in various forms of biodegradable and biocompatible biomaterials for use in various fields of medicine, surgery and tissue engineering.

Among the amide derivatives reported in the state of the art are known water-insoluble compositions constituted by mixtures deriving from the reaction between the carboxyl of hyaluronic acid, a nucleophil, such as an aminic compound, and an activating agent (U.S. Pat. No. 5,760,200; U.S. Pat. No. 4,937,270). Such mixtures are mainly used in the prevention of post-surgical adhesions.

U.S. Pat. No. 5,733,891 describes pharmaceutical compositions containing amide derivatives of hyaluronic acid obtained by reaction of its carboxyls with basic anti-tumour agents. The purpose of these compounds is to focus the action of the active principle on the diseased tissues and to limit any harmful effects on the healthy tissues.

Moreover, there are known amides of glycosaminoglycans, such as hyaluronic acid, with photosensitive compounds bound by polyfunctional compounds that act as bridges in the formation of amide bonds (U.S. Pat. No. 5,462,976).

Lastly, there is a known process for the preparation of insoluble amides by the reaction of active esters of hyaluronic acid with amines. (WO 95/24429).

The aim of the present invention is to provide isolated and characterized amides of hyaluronic acid or derivatives thereof, obtained by reacting the carboxy groups or amino groups originating from deacetylation reactions, with amines and acids of the aliphatic, aromatic, arylaliphatic, cycloaliphatic, heterocyclic series respectively, and without the use of spacer chains.

Said compounds can be either water soluble or insoluble, according to the acid, the amine, the percentage of amide bond or the derivative of hyaluronic acid used to prepare the amide.

Therefore, the products according to the present invention are suitable for a large number of applications according to their solubility in water, their viscosity and the stability of the amide bond.

Indeed, said compounds can be used to prepare both pharmaceutical compositions and biomaterials. Moreover, they have the advantage of being able to be formed by reaction, not only with amines, but also with pharmacologically active acids.

DETAILED DESCRIPTION OF THE INVENTION

Figure 1:
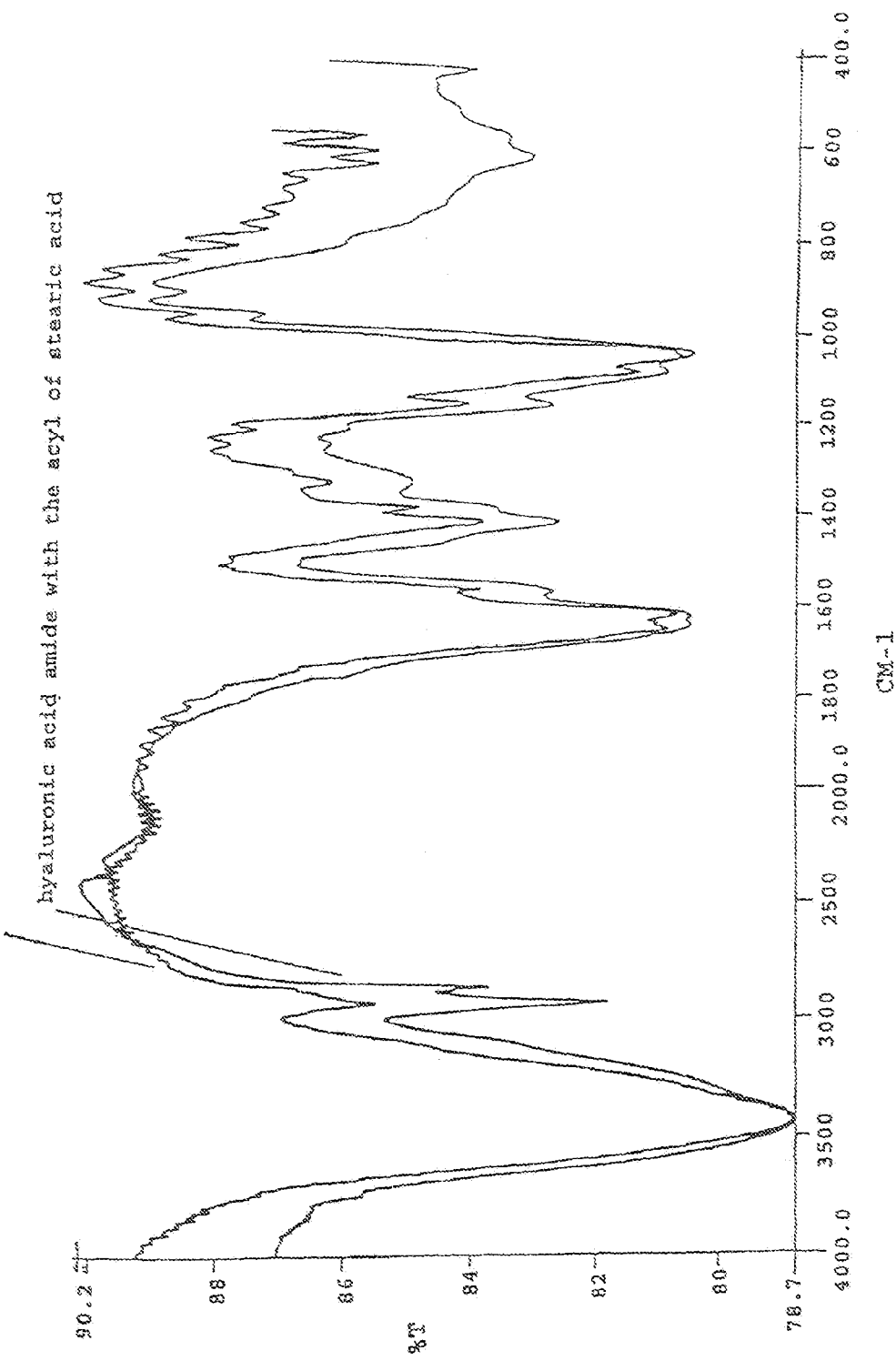
FIG. 1 shows the IR spectroscopy analysis of the compound of Example 11.

The present invention is directed to amides of hyaluronic acid and derivatives thereof for the preparation of pharmaceutical formulations, biomaterials and for the coating of biomedical objects and the process for their preparation.

The amides according to the present invention can be represented by the following general formula that represents the repetitive unit of the polymer:

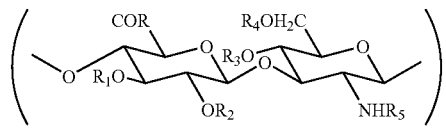

wherein:

$R=NR_6R_7$, or alcoholic group of the aliphatic, aromatic, arylaliphatic, cycloaliphatic, heterocyclic series, OH, O—, alcoholic group of hyaluronic acid, amino group of deacylated hyaluronic acid;

$R_1$, $R_2$, $R_3$, $R_4$,=H, $SO_{3-}$, acyl group derived from a carboxylic acid of the aliphatic, aromatic, arylaliphatic, cycloaliphatic, heterocyclic series, —CO—$(CH_2)_2$—COOY; Y=negative charge, or H;

$R_5$=—CO—$CH_3$, H, $SO_{3-}$, acyl group derived from a carboxylic acid of the aliphatic, aromatic, arylaliphatic, cycloaliphatic, heterocyclic series, acylic group of hyaluronic acid;

$R_6$=is H or a aliphatic, aromatic, arylaliphatic, cycloaliphatic, or heterocyclic group, substituted or unsubstituted;

$R_7$=is H or a aliphatic, aromatic, arylaliphatic, cycloaliphatic, or heterocyclic group, substituted or unsubstituted; wherein at least one of R or $R_5$ forms an amide group.

These are therefore amides obtained by reaction of an amine with a free carboxyl of hyaluronic acid or a derivative thereof, or by reaction of an acid with a deacylated amino group of hyaluronic acid or a derivative thereof Of the hyaluronic acid derivatives that can be used to prepare amides according to the present invention, the following are preferred:

hyaluronic acid esters wherein a part or all of the carboxy functions are esterified with alcohols of the aliphatic, aromatic, arylaliphatic, cycloaliphatic, heterocyclic series (EP 0216453 B1);—autocross-linked esters of hyaluronic acid wherein a part or all of the carboxy groups are esterified with the alcoholic functions of the same polysaccharide chain or other chains (EP 0341745 B1);

the cross-linked compounds of hyaluronic acid wherein a part or all of the carboxy groups are esterified with polyalcohols of the aliphatic aromatic, arylaliphatic, cycloaliphatic, heterocyclic series, generating cross-linking by means of spacer chains (EP 0265116 B 1);

hemiesters of succinic acid or the heavy metal salts of the hemiester of succinic acid with hyaluronic acid or with partial or total esters of hyaluronic acid (WO 96/357207); the 0-sulphated derivatives (WO 95/25751) or N-sulphated derivatives (PCT/EP98/01973).

Of the amides obtained by reaction of an amine on the carboxyl of hyaluronic acid or of a derivative thereof, of particular interest are the water-soluble ones.

By amide is meant a group of the formula —CON=.

Aliphatic means acyclic or pertaining to open-chain or branched carbon compounds such as alkanes, alkenes or alkynes. Examples of an aliphatic moiety include but are not limited to $C_1$-$C_{20}$ noncyclic hydrocarbons and their isomers such as methyl, ethyl, propyl, isopropyl, n-butyl, tert-butyl, isobutyl, pentyl, isopentyl, neopentyl, tert-pentyl, 2methylbucyl, 1,2-dimethylpropyl, hexyl, isohexyl, 1-methylpentyl, 2 methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1ethylbutyl, 2-ethylbutyl, 1,1, 2-trimethylpropyl, 1,2,2-trimethylpropyl, heptyl, octyl, nonyl, decyl, undecyl, dodecyl, tridecyl, tetradecyl, pentadecyl, hexadecyl, cetyl, heptadecyl, octadecyl, nonadecyl, stearyl, etc.

Aromatic means an aryl moiety having one or more unsaturated rings, each ring usually having 5 to 8 members and preferably 5 to 6 members.

Examples of the aromatic moiety include but are not limited to benzyl, toluyl, napthalyl, anthracenyl, phenanthryl, fluorenyl, coronenyl, triphenylenyl, fluoranthenyl, benzofluoranthenyl, benzopyrenyl, and pyrenyl.

Cycloaliphatic pertains to a carbon ring structure, usually having 3 to 8 members and preferably 5 to 6 members, that does not contain a resonance structure. Examples of cycloaliphatic groups include but are not limited to cycloalkanes and cycloolefins such as cyclopropyl, cyclobutyl, cyclopentyl, cyclohexyl, cycloheptyl, cycloactyl, cyclohexenyl (tetrahydrobenzenyl), cyclohexylidenyl, and cyclooctadienyl.

The heterocyclic series pertains to dissimilar atoms in a ring. A heterocyclic group is a heteroaryl group usually having a 3- to 8-membered, preferably 5- to 6-membered ring or fused ring containing at least one hetero atom (such as O, S, N, etc.) and include but are not limited to thienyl, furanyl, pyranyl, 2H-pyrrolyl, pyrrolyl, imidazolyl, pyrazolyl, pyridyl, pyrazinyl, pyrimidyl, pyridazinyl, isothiazolyl, isoxazolyl, furazanyl, benzothienyl, isobenzofuranyl, chromenyl, indolindinyl, isoindolyl, indolyl, purinyl, quinolidinyl, isoquinolyl, quinolyl, phthalazinyl, quinazolyl, carbazolyl, acridinyl, and phenanthridinyl.

An arylalkyl group is a group having both aromatic and aliphatic substituents as defined above. Examples of arylalkyl groups include but are not limited to ethylbenzenyl, isobutylbenzeneyl, benzyl, ethylbenzyl, propylbenzyl, isopropylbenzyl, butylbenzyl, isobutylbenzyl, cyclohexylbenzyl, styrenyl, and biphenyl.

An acyl group is an organic radical derived from an organic acid by the removal of a hydroxy group. Examples of acyl groups include but are not limited to formyl, acetyl, proprionayl, butyryl, valeryl, isovaleryl, pivaloyl; aroyl such as benzenesufonyl, benzoyl, toluoyl, and napthoyl; diacyl groups such oxalyl and succinic anhydride; and heteroaroyls such as furoyl, nicotnoyl, isonicotinoyl, etc.

Such amides can be used to advantage for the preparation of pharmaceutical compositions, for example in the form of gels, for the transport and release of drugs or biologically active substances for use in viscoelastic surgery or in ophthalmic surgery.

The amides according to the present invention can be salified with the heavy metals on the free or sulphuric carboxy groups, meaning by heavy metals the elements of the $4^{th}$, $5^{th}$ and $6^{th}$ periods of the periodical table such as silver, iron, cobalt, copper, zinc, arsenic, strontium, zirconium, antimony, gold, cesium, tungsten, selenium, platinum, ruthenium, bismuth, tin, titanium and mercury. Said salts can be used in dermatology, in ophthalmology, in dentistry, stomatology, rheumatology, urology, gynaecology, internal surgery, as food supplements, anti-oxidating, anti-rheumatic, anti-tumoural, anti-inflammatory, analgesic and anti-ulcer agents.

Moreover, the amide derivatives can be obtained by reaction of carboxyl or deacylated nitrogen of hyaluronic acid or a derivative thereof with an amine or with a pharmacologically active acid respectively, or they may be salified or simply associated with said compounds.

Of the pharmacologically active substances, the following are preferred:

antibiotics, anti-infective, antimicrobial, antiviral, cytostatic, cytotoxic, anti-tumoral, anti-inflammatory and wound healing agents, anesthetic, analgesics, vasoconstrictors, cholinergic or adrenergic agonists and antagonists, anti-thrombotic, anti-coagulant, haemostatic, fibrinolytic and thrombolytic agents) proteins and their fragments, peptides and polynucleotides.

Hereafter we report some examples of pharmacologically active substances belonging to the aforesaid classes of drugs.

antibiotics: amino glucosides, macrolides, tetracycline, peptides such as gentamicin, neomycin, streptomycin, dihydrostreptomycin, kanamycin, amikacin, tobramycin, spectinomycin, erythromycin, oleandomycin, carbomycin, spiramycin, oxytetrarycline, rolitetracycline, bacitracin, polymyxin B, gramicidin, colistin, chloramphenicol, lincomycin, vancomycin, novobiocin, ristocetin, clindamycin, amphotericin B, griseofulvin, nostatin and their salts;

anti-infective agents: diethylcarbamazine, mebendazole, sulfamides such as sulfacetamide, sulfadiazine, sulfisoxazole;

anti-virals and anti-tumorals: iodoxuridine, adenine, adenine arabinoside, trifluorothymidine, acyclovir, ethyldeoxyuridine, bromovinyldeoxyuridine, 5-iodo-5'-amino-2',5'-dideoxyuridine;

steroid anti-inflammatory agents: dexamethasone, hydrocortisone, prednisolone, fluorometliolone, medrisone and their esters;

non-steroid anti-inflammatory agents: indomethacin, oxyphenbutazone, fluorbiprofene, dichlofenac, ibuprofen;

anesthetic: benoxinate, proparacaine, dibucaine, lidocaine, benzocaine, benzydamine, bupivacaine and their salts;

cholinergic agonists: pilocarpine, methacholine, carbamylcholine, aceclidine, physostigmine, neostigmine, demecarium and their salts;

cholinergic antagonists: atropine and its salts;

adrenergic agonists: noradrenalin, adrenalin, naphazoline, methoxamine and their salts;

adrenergic antagonists: propanol timolol, pindolol, bupranolol, athenolol, methoprolol, oxprenolol, practolol, butoxamine, sotalol, butadrinc, labctalol and their salts;

antibacterials and disinfectants: nitrofurazone, mafenide, chlorhexidine, the derivatives of 8-hydroxyquinolinc and their salts;

cytotoxics: fluorouracil, methotrexate, podophyllin.

Of particular interest are the forms for the transport and release of the above said substances and of biologically active substances such as proteins and their fragments, peptides, polynucleotides, growth factors, enzymes, vaccines, substances used in the treatment of diseases associated with genetic defects such as those depending on enzymatic hypo- or hyper-activity due to defects of the gene encoding for a given enzyme, deforming diseases and hereditary diseases.

The amide derivatives according to the present invention, in association with radioactive and non-radioactive substances, used in contrast systems, can be used as markers in in vivo diagnostics, for the identification and treatment of tumour tissues or damaged tissues.

One considerable advantage is represented by the possibility of processing the amide compounds and their salts in different forms of biomaterials such as sponges, films, membranes, threads, tampons, nonwoven fabric, microspheres, nanospheres, gauzes, gels and guide channels. Said biomaterials, used in one or more associated forms, may be constituted by one or more amide derivatives and their salts, optionally in association with other natural, synthetic or semisynthetic polymers, and optionally, with biologically active substances.

Some examples of natural polymers that can be used are collagen, coprecipitates of collagen and glycosaminoglycans, cellulose, polysaccharides in the form of gels such as chitin, chitosan, pectin or pectic acid, agar, agarose, xanthane, gellan, alginic acid or the alginates, polymannans or polyglycans, starch and natural gums.

Semisynthetic polymers, for example, can be chosen from the group consisting of collagen cross-linked with agents such as aldehydes or precursors of the same, dicarboxylic acids or their halogenides, diamines, derivatives of cellulose, hyaluronic acid, chitin or chitosan, gellan, xanthane, pectin or pectic acid, polyglycans, polymannan, agar, agarose, natural gum or glycosaminoglycans.

Lastly, examples of synthetic polymers that can be used are polylactic acid, polyglycolic acid or copolymers of the same or their derivatives, polydioxanes, polyphosphazenes, polysulphonic resin, polyurethanes, PTFE.

The above said biomaterials can be used to advantage in various fields of surgery, such as in internal and osteo-articular surgery, neuro-surgery, anastomotic, viscoelastic, ophthalmic, oncological, plastic and aesthetic, otorhinolaryngological, abdominal and pelvic, urogynaecological, cardiovascular surgery, in the prevention of post-surgical adhesions and hypertrophic scarring.

Moreover, the amide compounds in association with fibrin, and optionally other biologically active substances, can be used for the preparation of surgical glues.

The biomaterials according to the present invention can be used not only in the field of surgery but also in haemodyalisis, cardiology, dermatology, ophthalmology, otorhinolaryngology, dentistry, orthopaedics, gynaecology, urology, in extracorporeal blood circulation and oxygenation, in cosmetics and in angiology.

Said biomaterials, in their various forms, can be used to advantage as scaffolds on which to grow cells such as mesenchymal cells or mature cells to obtain connective, glandular and nerve tissue.

These biopolymers can also be used in the processes of coating objects used both in the medical field and in industrial sectors, giving new biological characteristics to the surfaces of the material used as a support.

Examples of the objects that can be coated are: catheters, guide channels, probes, cardiac valves, soft tissue prostheses, prostheses of animal origin such as cardiac valves from pigs, artificial tendons, bone and cardiovascular prostheses, contact lenses, blood oxygenators, artificial kidneys, hearts) pancreas) and livers, blood bags) syringes, surgical instruments, filtration systems, laboratory instruments, containers for cultures and for the regeneration of cells and tissues, supports for peptides, proteins and antibodies.

The process of coating the surface of such objects can be performed, for example by the
Plasma Coating technique, described in the international patent application by the Applicant, publication No. W096/24392.

The process for the preparation of amides on the nitrogen of hyaluronic acid or one of its deacetylated derivatives can be summarised as the following steps:

deacetylation reaction, for example, by reaction with hydrazine sulphate (J. Riesenfeld, Analy. Bioch. 1990, vol. 188, pp 383-389); preparation of the quaternary ammonium salt of the deacetylated compound such as the tetrabutylammonium salt;

preparation of the acylating agent in the form of an active ester, for example, of paranitrophenylester of aliphatic, aromatic, arylaliphatic, cycloaliphatic or heterocyclic acid, chosen for the formation of the amide;

N-acylation reaction between the quaternary ammonium salt of hyaluronic acid or of one of its deacetylated derivatives and the acylating agent.

The compound is analytically characterised by the following methods: analysis of the percentage of free amino groups:

the method described by J. Riesenfeld (Analy. Bioch. 1990, vol. 188, pp 383-389);

mean molecular weight:

this is determined by GPC using a set of Shadex B-803 and B-806 columns, and RI and MALLS equipment;

IR and UV spectroscopy analysis:

TLC analysis.

The sample is hydrolysed in a 1 mol. solution of sodium hydroxide for 2-4 hours at 70° C. and then acidified with a 1 mol. solution of hydrochloric acid. The acid that is released during hydrolysis is extracted with organic solvent. The dry organic extract is analysed by HPLC.

% of N-acylation (hydrolysis of the amide)

two types of analysis are performed to measure the percentage of N acylated groups:

a) the method described by J. Riesenfeld (Analy. Bioch. 1990, vol. 188, pp 383-389);

b) the sample is hydrolysed in a 1 mol. solution of sodium, hydroxide for 2-4 hours at 70° C. and then acidified with a 1 mol. solution of hydrochloric acid. The acid that is released during hydrolysis is extracted with organic solvent. The dry organic extract is analysed by HPLC.

Preparation of the amides on the carboxyl of hyaluronic acid or a derivative thereof consists in activating the carboxy groups by reaction of the same, in acid form or in the form of quaternary ammonium salt, with an agent such as carbonyldiimidazole, which converts carboxylic acid in the reactive form of an acylating agent.

Said reaction can be performed by catalysis with hydrochloric acid or acid resin and with an amine of the aliphatic, aromatic, arylaliphatic, cycloaliphatic and heterocyclic series.

Characterisation of the compounds includes the following methods:

IR and UV spectroscopy:
Chromatographic analysis.
The sample is hydrolysed in a 1 mol. solution of sodium hydroxide for 2-4 hours at 70° C. and the amine that is released during hydrolysis is extracted with organic solvent. The dry organic extract is analysed by HPLC.

The percentage of amidation of the product is generally in the range of about 1% to about 90%, more preferably in the range of about 5% to about 60%, and most preferably in the range of about 20% to about 50%.

Example 1

Preparation of Partially N-Deacetylated Hyaluronic Acid in the Form of Sodium Salt (DHA/Na)

One gram of sodium hyaluronate, with a mean molecular weight of 600 Kda, is solubilised in 50 ml of a 1% solution of hydrazine sulphate in hydrazine monohydrate.

This is left to react under agitation for five days (120 hours) at 55° C., after which the reaction is stopped by adding 100 ml of ethanol.

The precipitate thus formed is filtered through a Gooch crucible, washed with ethanol and then dried at room temperature at reduced pressure.

Any hydrazide of hyaluronic acid that will probably be fanned during the reaction with hydrazinolysis is destroyed by reaction with $HIO_3$ (iodic acid). As the reaction may be very vigorous, it is conducted while cooling the reaction container in iced water.

The product of hydrasinolysis is solubilised in 50 ml of a solution of 5% sodium acetate and reacted with 25 ml of a 0.5 M solution of iodic acid.

The reaction proceeds for 30 minutes under agitation, after which 5 ml of a 57% solution of HI is added to destroy any unreacted $HIO_3$.

The iodine that has formed is extracted from the aqueous solution with at least three 30-ml aliquots of ethyl ether (until complete decolouring of the aqueous phase). The aqueous solution is brought to neutral pH by adding a solution of NaOH 0.5M followed by treatment with 100 ml of ethanol.

The precipitate obtained is filtered with a Gooch crucible, washed with ethanol and then dried at room temperature and at reduced pressure.

The product obtained is characterised analytically to determine the percentage of N-dcacetylated groups and the mean molecular weight.

| | |
|---|---|
| Yield of the reaction | 90% |
| % of N-deacetylation | 26% |
| mean molecular weight | 130 Kda |

Example 2

Preparation of the Salt of Hyaluronic Acid Partially N-Deacetylated with Tetrabutylammonium (DHAITBA).

One gram (2.5 mmol.) of hyaluronic acid sodium salt, partially N-deacetylated, is solubilised in 60 ml of water and the solution is percolated through a column filled with 25 ml of a sulphonic resin in the form of tetrabutylammonium salt (TBA). The sulphonic resin in H form is activated with a 40% solution w/v of TBAOH.

The eluate, containing N-deacetylated hyaluronic acid TBA salt is collected and freeze-dried.

Example 3

Preparation of p-$NO_2$-Phenylester of Benzoic Acid (Acylating Agent)

Ten grams (0.082 mol.) of benzoic acid is solubilised in 800 ml of $CH_2Cl_2$, after which 11.4 g (0.082 mol.) of p-$NO_2$-phenol and 16.9 g (0.082 mol) of DCC (Dicyclohexylcarbodiimide) are added. The reaction proceeds for 2 hours, while the solution is boiled and refluxed.

Subsequently, the dicyclohexylurea that forms is filtered and the filtered product is dried with a rotavapor under reduced pressure. The product thus obtained is purified by repeated crystallisation in ethyl acetate. The crystals are filtered and placed to dry at room temperature at reduced pressure.

The derivative is characterised by TLC analysis (eluent: $CH_2Cl_2$/ethyl acetate 90/10 and Rf=0.77) and by IR and UV spectroscopy.

| | |
|---|---|
| Yield of the reaction | 92% |

Example 4

Preparation of p-$NO_2$-Phenylester of Cinnamic Acid (Acylating Agent)

Twelve grams (0.082 mol.) of cinnamic acid is solubilised in 800 ml of $CH_2Cl_2$, after which 11.4 g (0.082 mol.) of p-$NO_2$-phenol and 16.9 g (0.082 mol) of DCC (Dicyclohexylcarbodiimide) are added. The reaction proceeds for 2 hours during which time the solution is boiled and refluxed.

Subsequently, the dicyclohexylurea is filtered and the filtered product is dried using a rotavapor at reduced pressure. The product obtained is purified by repeated crystallisation in ethanol, the crystals are filtered and left to dry at room temperature and reduced pressure.

The derivative is characterised by TLC analysis (eluent: $CH_2Cl_2$/ethyl acetate 90/10 and Rf=0.77) and by IR and UV spectroscopy.

| | |
|---|---|
| Yield of the reaction | 89% |

Example 5

Preparation of p-$NO_2$-Phenylester of Dodecanoic Acid (Acylating Agent)

Sixteen grams of dodecanoic acid is solubilised in 1 litre of $CH_2Cl_2$, after which 11.4 g (0.082 mol.) of p-$NO_2$-phenol and 16.9 g (0.082 mol.) of DCC (Dicyclohexylcarbodiimide) are added. The reaction proceeds for 2 hours during which time the solution is boiled and refluxed.

Subsequently, the dicyclohexylurea is filtered and the filtered product is dried using a rotavapor at reduced pressure. The product obtained is purified by repeated crystallisation in ethyl acetate, the crystals are filtered and left to dry at room temperature and at reduced pressure.

The derivative is characterised by TLC analysis (eluent: $CH_2Cl_2$/ethyl acetate 90/10 and Rf=0.77) and by IR spectroscopy.

| | |
|---|---|
| Yield of the reaction | 93% |

Example 6

Preparation of p-$NO_2$-Phenylester of Stearic Acid (Acylating Agent)

23.3 grams of stearic acid is solubilised in 1 litre of $CH_2Cl_2$, after which 11.4 g (0.082 mol.) of p-$NO_2$-phenol and 16.9 g (0.082 mol.) of DCC (Dicyclohexylcarbodiimide) are added. The reaction proceeds for 2 hours during which time the solution is boiled and refluxed.

Subsequently the dicyclohexylurea is filtered and the filtered product is dried using a rotavapor at reduced pressure. The product obtained is purified by repeated crystallisation in absolute ethanol, the crystals are filtered and left to dry at room temperature at reduced pressure.

The derivative is characterised by TLC analysis (eluent: $CH_2Cl_2$/ethyl acetate 90/10 and Rf=0.82) and by IR spectroscopy.

| | |
|---|---|
| Yield of the reaction | 87% |

Example 7

Preparation pf p-$NO_2$-Phenylester of o-acetyl Salicylic Acid (Acylating Agent)

14.7 g of acetylsalicylic acid is solubilised in 1 litre of $CH_2Cl_2$, after which 11.4 g (0.082 mol.) of p-$NO_2$-phenol and 16.9 g (0.082 mol.) of DCC (Dicyclohexylcarbodiimide) are added. The reaction proceeds for 2 hours during which time the solution is boiled and refluxed.

Subsequently, the dicyclohexylurea that forms is filtered and the filtered product is dried using a rotavapor at reduced pressure. The product obtained is purified by repeated crystallisation in absolute ethanol, the crystals are filtered and left to dry at room temperature at reduced pressure.

The derivative is characterised by TLC analysis (eluent: $CH_2Cl_2$/ethyl acetate 90/10 and Rf=0.82) and by IR spectroscopy.

| | |
|---|---|
| Yield of reaction | 80% |

Example 8

Preparation of Partially N-Acylated Hyaluronic Acid (with the Benzoic Acid Derivative)

One gram (1.6 mmol.) of DHA/TBA (26% deacetylation) is solubilised in 50 ml of DMSO, after which 5 ml of a 10% solution of p-$NO_2$-phenylester of benzoic acid (prepared according to example 3) in DMSO is added. The reaction proceeds for 24 hours, under agitation at room temperature, after which it is blocked by adding 2.5 ml of a saturated solution of NaCl.

This is left to react for 30 minutes and then 100 ml of ethanol is slowly added. The precipitate thus obtained is filtered through a Gooch, washed with ethanol and ethyl ether and lastly dried at room temperature and at reduced pressure.

The derivative is analysed by TLC (after hydrolysis of the amide), colorimetric analysis of the percentage of free $NH_2$ groups and IR and UV spectroscopy.

| | |
|---|---|
| Yield of the reaction | 85% |
| % free $NH_2$ | 11% |
| % N-acylation | 15% |

Example 9

Preparation of Partially N-Acylated Hyaluronic Acid (with the Derivative of Cinnamic Acid)

One gram (1.6 mmol.) of DHA/TBA (26% deacetylation) is solubilised in 50 ml of NMP, after which 10 ml of a 10% solution of p-$NO_2$-phenylester of cinnamic acid (prepared according to example 4) in NMP is added. The reaction proceeds for 24 hours, under agitation, at room temperature, after which it is blocked by adding 2.5 ml of a solution saturated with NaCl. This is left to react for 30 minutes and lastly 100 ml of ethanol is slowly added. The precipitate thus obtained is filtered through a Gooch crucible, washed with ethanol/water 9:1, ethyl ether and lastly dried at room temperature at reduced pressure.

The derivative is analysed by TLC (after hydrolysis of the amide), colorimetric analysis of the percentage of free $NH_2$ groups and IR and UV spectroscopic analysis.

| | |
|---|---|
| Yield of the reaction | 85% |
| % free $NH_2$ | 11% |
| % N-acylation | 15% |

Example 10

Preparation of Partially N-Acylated Hyaluronic Acid (with a Derivative of Dodecanoic Acid)

One gram (1.6 mmol.) of DHA/TBA (26% deacetylation) is solubilised in 50 ml of NMP, after which 3.2 ml of a 10% solution of p-$NO_2$-phenylester of dodecanoic acid (prepared according to example 5) in NMP is added.

The reaction proceeds for 24 hours, under agitation, at room temperature, after which it is blocked by adding 2.5 ml of a saturated solution of NaCl.

This is left to react for 30 minutes, after which 100 ml of ethanol is gently added. The precipitate obtained is filtered through a Gooch, washed with ethanol and ethyl ether and lastly dried at room temperature at reduced pressure.

The derivative is analysed by TLC (after hydrolysis of the amide), colorimetric analysis of the percentage of free $NH_2$ groups and IR and UV spectroscopy.

| | |
|---|---|
| Yield of the reaction | 88% |
| % free $NH_2$ | 10% |
| % N-acylation | 16% |

Example 11

Preparation of Partially N-Acylated Hyaluronic Acid (with the Derivative of Stearic Acid)

One gram (1.6 mmol) of DHA/TBA (26% deacetylation) is solubilised in 50 ml of NMP, after which 6 ml of a 10% solution of p-NO$_2$-phenylester of stearic acid (prepared according to example 6) in NMP is added. The reaction proceeds for 24 hours under agitation at room temperature after which it is blocked by adding 2.5 ml of a saturated solution of NaCl. This is left to react for 30 minutes and then 100 ml of ethanol is slowly added.

The precipitate thus obtained is filtered through a Gooch filter, washed with ethanol and ethyl ether and lastly left to dry at room temperature and reduced pressure.

The derivative is analysed by TLC (after hydrolysis of the amide), colorimetric analysis of the percentage of free NH$_2$ groups and IR and UV spectroscopy.

| | |
|---|---|
| Yield of the reaction | 85% |
| % free NH$_2$ | 12% |
| % N-acylation | 14% |

IR spectroscopy (FIG. 1): the figure shows the difference between the IR spectrum of the amide and that of hyaluronic acid sodium salt. In the spectrum of the amide, there is an evident peak in the area of 2900 cm-1, due to the stretching of the CH$_2$ of the stearate.

Example 12

Preparation of Partially N-Acylated Hyaluronic Acid (with Acetyl Salicylic Acid Derivative)

One gram (1.6 mmol.) of DHA/TBA is solubilised in 50 ml of NMP, after which 3.2 ml of a 10% solution of p-N02-phenylester of acetyl salicylic acid (prepared according to example 7) in NMP is added. The reaction proceeds for 24 hours under agitation at room temperature, after which it is blocked by adding 2.5 ml of a saturated solution of NaCl. This is left to react for 30 minutes and lastly 100 ml of ethanol is slowly added. The precipitate thus obtained is filtered through a Gooch crucible, washed with ethanol and ethyl ether and then dried at room temperature and reduced pressure.

The derivative is analysed by TLC (after hydrolysis of the amide), colorimetric analysis of the percentage of free NH$_2$ groups and IR and UV spectroscopy.

| | |
|---|---|
| Yield of the reaction | 90% |
| % free NH$_2$ | 10% |
| % N-acylation | 16% |

Example 13

Preparation of Benzylamide of Hyaluronic Acid

Two grams (3.2 mmol.) of tetrabutylammonium salt of hyaluronic acid (HA/TBA) is solubilised in 100 ml of DMSO. This solution is supplemented with 3 ml of humid acid resin in DMSO and 784 mg (4.8 mmol.) of 1,1-carbonyldiimidazole. This is left to react under agitation for 12 hours, after which it if filtered through a Gooch crucible to eliminate the resin and the filtered product is supplemented with 1 ml (9.6 mmol) of benzylamine. This is left to react for 48 hours and then 5 ml of a saturated solution of NaCl is added and it is left under agitation for 30 minutes. It is supplemented with 200 ml of acetone and the precipitate thus obtained is filtered and dried at reduced pressure.

The dry derivative is characterised by TLC, IR and HPLC analysis.

| | |
|---|---|
| % of amidation | 25% |

Figure 2:
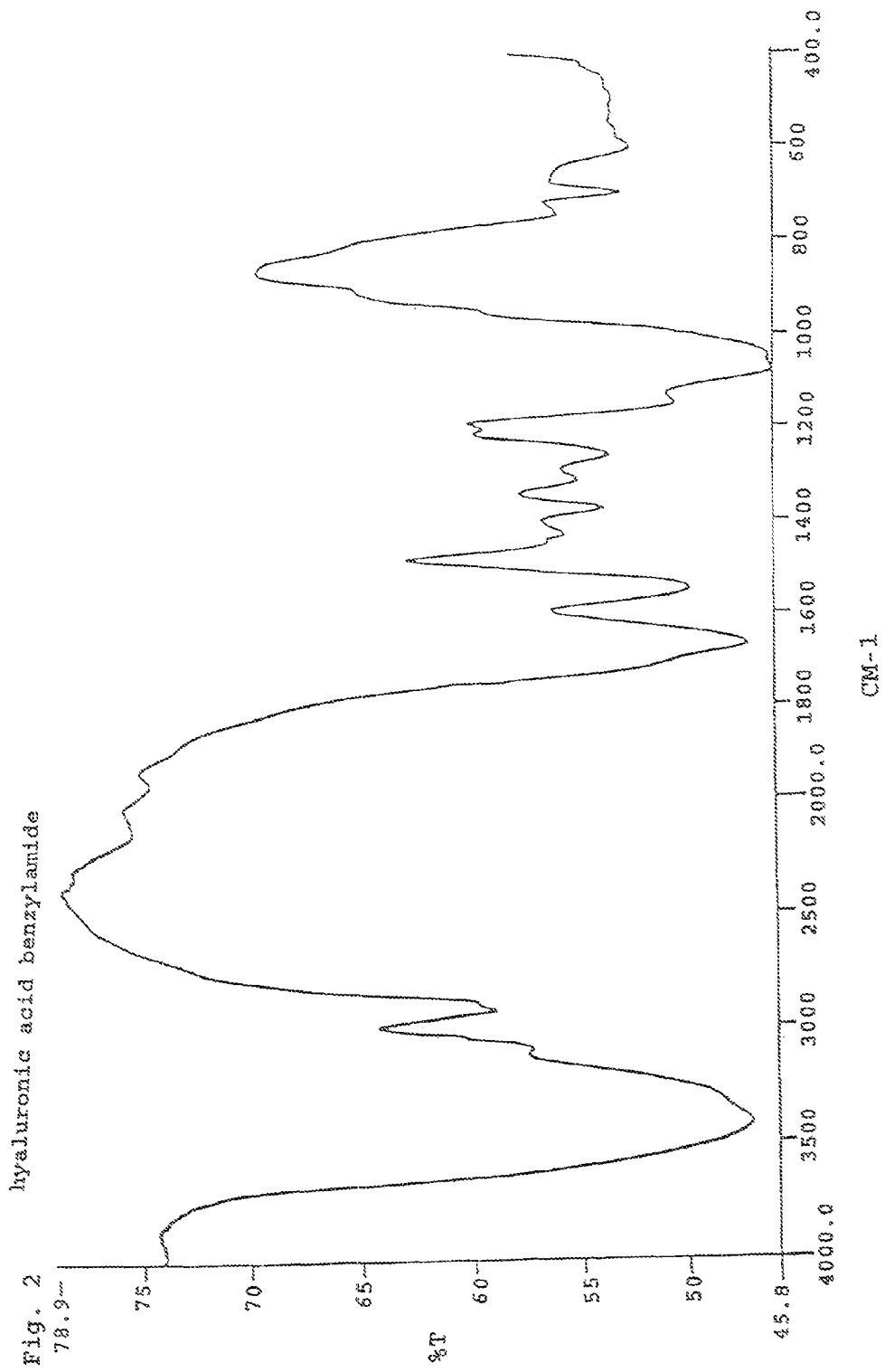
FIG. 2 shows the IR spectroscopy analysis of the compound of Example 13, and shows a peak at 1537 cm-1 due to bending in the NH plane (the amide band) and a peak at about 730 cm-1 due to bending of the CH outside the plane of the aromatic ring.
Figure 3:
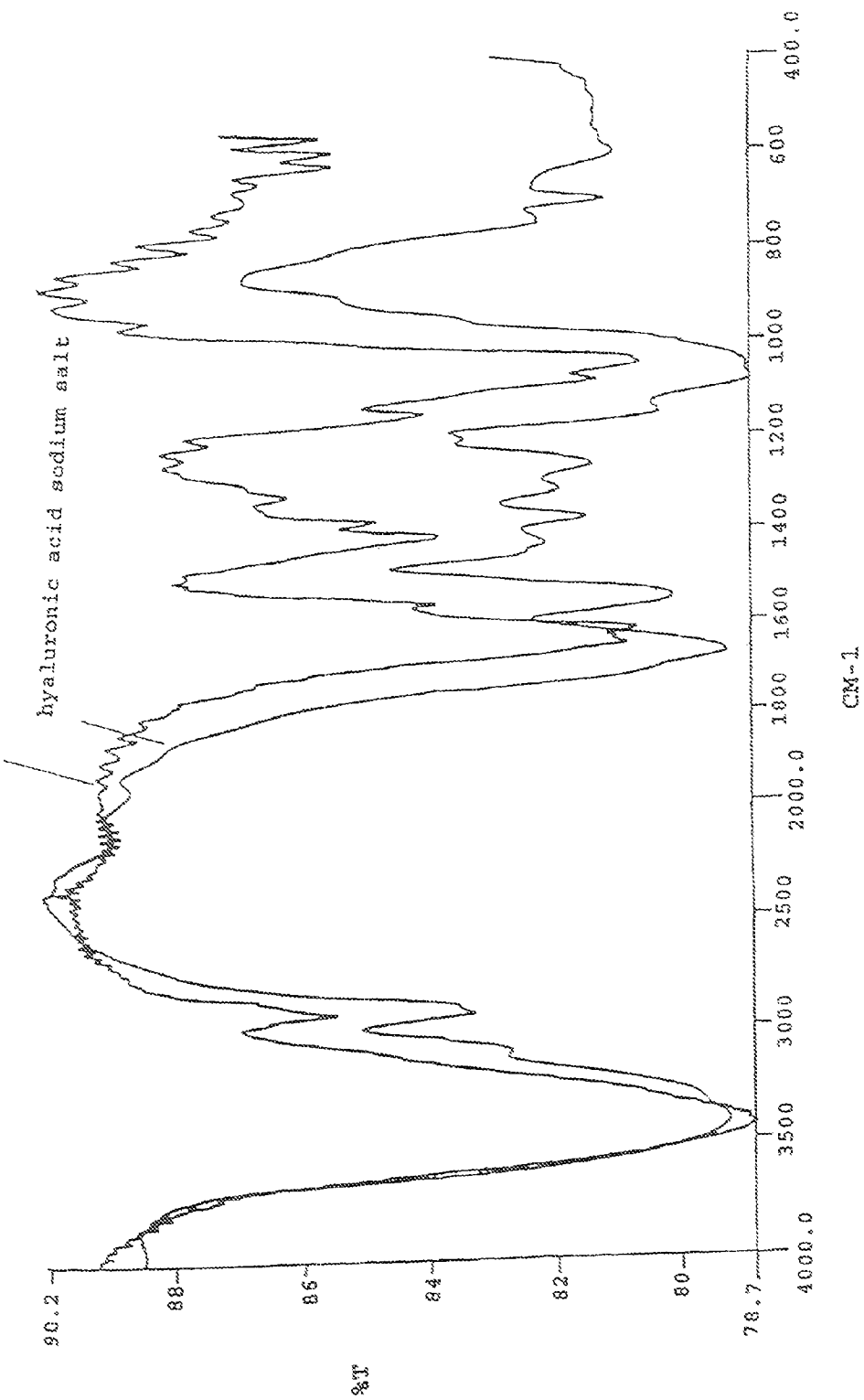
FIG. 3 shows the IR spectroscopy analysis of the compound of Example 13 and shows the difference between the graph relative to the amide and that of the sodium salt of hyaluronic acid.

IR spectroscopy (FIGS. 2 and 3): the spectrum in FIG. 2 clearly shows a peak at 1537 cm-1 due to bending in the NH plane (the amide band) and a peak at about 730 cm-1 due to bending of the CH outside the plane of the aromatic ring. FIG. 3 shows the difference between the graph relative to the amide and that of the sodium salt of hyaluronic acid.

Example 14

Preparation of Benzylamide of Hyaluronic Acid

Two grams (3.2 mmol.) of tetrabutylammonium salt of hyaluronic acid (HA/TBA) is solubilised in 100 ml of DMSO. The solution is adjusted to pH 3 with HCl 1M and then 784 mg (4.8 mmol.) of 1,1-carbonyldiimidazole is added. This is left to react under agitation for 12 hours, then it is filtered through a Gooch crucible to eliminate the resin and 1 ml (9.6 mmol.) of benzylamine is added to the filtered product. This is left to react for 48 hours, then 5 ml of a saturated solution of NaCl is added and left under agitation for 30 minutes. To this is added 200 ml of acetone, the precipitate thus obtained is filtered and dried under reduced pressure.

The dry derivative is characterised by TLC, IR and HPLC analysis.

| | |
|---|---|
| % amidation | 15% |

Example 15

Preparation of Benzylamide of Hyaluronic Acid

Two grams (5.2 mmol.) of hyaluronic acid in acid form is solubilised in 100 ml of DMF. To this solution is added 854 mg (5.2 mmol.) of 1,1-carbonyldiimidazole. This is left to react under agitation for 6 hours, after which 1.13 ml (10.4 mmol.) of benzylamine is added. The reaction proceeds for 48 hours, and is then blocked by adding 200 ml of acetone.

The precipitate thus obtained is filtered and dried under reduced pressure.

The dry derivative is characterised by TLC, IR and HPLC analysis.

| | |
|---|---|
| % amidation | 60% |

Example 16

Preparation of Benzylamide of Hyaluronic Acid

Two grams (5.2 mmol.) of hyaluronic acid in acid form is solubilised in 100 ml of DMF. To this solution is added 2 ml of pyridine, 3.68 g (0.026 mol,) of p-NO$_2$-phenol and pyridine chloride until a pH of 7/8 is reached.

Lastly, 5.3 (0.026 mol.) of DCC and 2.8 (0.026 mol.) of benzylamine are added. This is left to react under agitation for 16 hours after which the reaction is blocked by adding 200 ml of acetone. The precipitate thus obtained is filtered and dried under reduced pressure.

The dry derivative is characterised by TLC, IR and HPLC analysis.

| % amidation | 5% |
|---|---|

Example 17

Preparation of Benzylamide of Hyaluronic Acid

Two grams (3.2 mmol.) of HA/TBA is solubilised in 100 ml of DMSO. The solution is insufflated with gaseous HCl until the reaction mixture reaches a pH of between 4.5 and 5. Subsequently, 518 mg (3.2 mmol.) of carbonyldiimidazole is added. It is left to react under agitation for one hour at room temperature, after which 0.700 ml (6.4 mmol.) of benzylamine is added. The reaction proceeds for 16-18 hours. After this time, 5 ml of a solution saturated with NaCl is added. It is precipitated by adding 200 ml of acetone and the precipitate thus obtained is filtered and dried under reduced pressure.

The dry derivative is characterised by TLC (after hydrolysis), IR and HPLC analysis.

| % amidation | 50% |
|---|---|

Example 18

Preparation of the Octylamide of Hyaluronic Acid

Two grams (3.2 mmol.) of HA/TBA is solubilised in 100 ml of DMSO. The solution is insufflated with gaseous HCl till the reaction mixture reaches a pH of between 4.5 and 5. Subsequently, 207 mg (1.28 mmol.) of carbonyldiimidazole is added. It is left to react under agitation for one hour at room temperature, after which 0.417 ml (3.2 mmol.) of octylamine is added. The reaction proceeds for 16-18 hours. At the end of this time, 5 ml of a solution saturated with NaCl is added. It is precipitated by adding 200 ml of acetone and the precipitate obtained is filtered and dried under reduced pressure.

The dry derivative is characterised by TLC (after hydrolysis), IR and HPLC analysis.

| % amidation | 25% |
|---|---|

Example 19

Preparation of the Dodecyl Amide of Hyaluronic Acid:

Two grams (3.2 mmol.) of HA/TBA is solubilised in 100 ml of DMSO. The solution is insufflated with gaseous HCl till the reaction mixture reaches a pH of between 4.5 and 5. Subsequently, 104 mg (0.64 mmol.) of carbonyldiimidazole is added. It is left to react, under agitation, for one hour at room temperature, after which 600 mg (3.2 mmol.) of dodecylamine is added. The reaction proceeds for 16-18 hours. After this time, 5 ml of a solution saturated with NaCl is added. It is precipitated by adding 200 ml of acetone and the precipitate obtained is filtered and dried under reduced pressure.

The dry derivative is characterised by TLC (after hydrolysis), IR and HPLC analysis.

| % amidation | 15% |
|---|---|

Example 20

Preparation of the Hexadecylamide of Hyaluronic Acid:

Two grains (3.2 mmol.) of HA/TBA is solubilised in 100 ml of DMSO. The solution is insufflated with gaseous HCl till the reaction mixture reaches a pH of between 4.5 and 5. Subsequently, 52 mg (0.32 mmol.) of carbonyldiimidazole is added and left to react under agitation for one hour at room temperature, after which 780 mg (3.2 mmol.) of hexadecylamine is added. The reaction proceeds for 16-18 hours. After this time, 5 ml of a solution saturated with NaCl is added. It is precipitated by adding 200 ml of acetone and the precipitate obtained is filtered and dried under reduced pressure.

The dry derivative is characterised by TLC (after hydrolysis), IR and HPLC analysis.

| % amidation | 5% |
|---|---|

The invention being thus described, it is clear that these methods can be modified in various ways. Such modifications are not to be considered as divergences from the spirit and purpose of the invention and any modification that would appear evident to an expert in the field comes within the scope of the following claims.

What is claimed:

1. A pharmaceutical composition or biomaterial comprising a water-soluble amide compound of hyaluronic acid or a derivative thereof which comprises at least one repetitive unit of the following general formula:

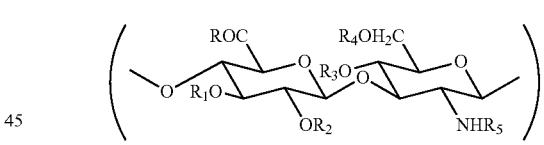

wherein:
R=NR$_6$R$_7$,
R$_1$, R$_2$, R$_3$, R$_4$=H;
R$_5$=CO—CH$_3$;
R$_6$=is H;
R$_7$=is a aliphatic, aromatic, arylaliphatic, cycloaliphatic, or heterocyclic group, substituted or unsubstituted,
with the proviso that R does not form an amide bond with a medicinal agent,
wherein said pharmaceutical composition comprises a pharmaceutically acceptable carrier.

2. Pharmaceutical compositions or biomaterials according to claim 1, wherein said amidic water-soluble compounds are obtained by reaction of the carboxylic groups of hyaluronic acid with an amino group of the aliphatic, aromatic, arylaliphatic, cycloaliphatic, or heterocyclic series, which is a 3- to 8-membered ring with at least one heteroatom selected from N, O and S.

3. Pharmaceutical compositions or biomaterials according to claim 1, wherein some or any carboxy groups on the hyaluronic acid derivatives are esterified with aliphatic, aromatic, arylaliphatic, cycloaliphatic, or heteroaliphatic alcohols.

4. Pharmaceutical compositions or biomaterials according to claim 1 or claim 2, wherein said amidic compounds are salified with one or more heavy metals.

5. Pharmaceutical compositions or biomaterials according to claim 4, wherein the heavy metals are those of the $4^{th}$, $5^{th}$ and $6^{th}$ group of the table of elements and preferably silver, cobalt, iron, copper, zinc, arsenic, strontium, zirconium, antimony, gold, cesium, tungsten, selenium, platinum, ruthenium, bismuth, tin, titanium and mercury.

6. Pharmaceutical compositions or biomaterials according to claim 1 or claim 2, wherein said amidic compounds are salified with pharmacologically active substances, wherein the pharmacologically active substances are antibiotics, anti-infective, antimicrobial, antiviral, cytostatic, antitumoral, anti-inflammatory, wound healing agents, anaesthetics, cholinergic or adrenergic agonists and antagonists, antithrombotic, anticoagulant, haemostatic, fibrinolytic, thrombolytic agents, proteins and their fragments, peptides, or polynucleotides.

7. A pharmaceutical composition according to claim 1 or claim 2 further comprising at least one pharmacologically active substance, wherein the pharmacologically active substances are antibiotics, anti-infective, antimicrobial, antiviral, cytostatic, antitumoral, anti-inflammatory, wound healing, anaesthetic agents, cholinergic or adrenergic agonists or antagonists, antithrombotic, anticoagulant, haemostatic, fibrinolytic, thrombolytic agents, proteins and their fragments, peptides, polynucletotides, growth factors, enzymes, or vaccines.

8. A pharmaceutical composition according to claim 1 or claim 2 further comprising at least one radioactive or non-radioactive diagnostic marker.

9. A biomaterial according to claim 1 or claim 2 further comprising at least one other natural, semisynthetic, or synthetic polymer.

10. Biomaterials according to claim 9, wherein the natural polymers are collagen, co-precipitates of collagen and glycosaminoglycans, cellulose, or polysaccharides in the form of gels.

11. Biomaterials according to claim 9, wherein the semi-synthetic polymers are cross-linked collagen, dicarboxylic acids or their halogenides, diamines, derivatives of cellulose, hyaluronic acid, chitin or chitosan, gellan, xanthane, pectin or pectic acid, polyglycans, polymannan, agar, agarose, natural gum or glycosaminoglycans.

12. Biomaterials according to claim 9, wherein the synthetic polymers are polylactic acid, polyglycolic acid or copolymers of the same or their derivatives, polydioxanes, polyphosphazenes, polysulphonic resins, polyurethanes, or PTFE.

13. Biomaterials according to claim 9, in association with fibrin, and optionally with other biologically active substances for the preparation of surgical glues, wherein the biologically active substances are proteins and their fragments, peptides, polynucleotides, growth factors, enzymes, or vaccines.

14. A scaffold for cell cultures comprising the biomaterials according to claim 9.

15. Surgical and health-care articles comprising the biomaterials according to claim 9.

16. Biomaterials according to claim 9, in the form of guide channels, gauzes, threads, gels, hydrogels, tampons, films, membranes, sponges, non-woven fabrics, microspheres, or nanospheres.

17. Surgical and health-care articles according to claim 15, in the form of guide channels, gauzes, threads, gels, hydrogels, tampons, films, membranes, sponges, non-woven fabrics, microspheres, or nanospheres.

18. A biomedical object selected from the group consisting of bypasses, venous catheters, shunts, catheters, guide channels, probes, cardiac valves, artificial tendons, bone and cardiovascular prostheses, contact lenses, soft tissue prostheses, prostheses of animal origin, blood oxygenators, artificial kidneys, hearts, pancreas and livers, blood bags, syringes, surgical instruments, filtration systems, laboratory instruments, containers for cell cultures and for the regeneration of cells and tissues, supports for peptides, proteins, antibodies, which has been coated with pharmaceutical composition or biomaterial an amidic compound of claim 1 or claim 2.

19. Process for the preparation of amidic compounds according to claim 1 having the amides on the carboxyl of hyaluronic acid or a derivative thereof, involving the following steps:
a) activation of the carboxy groups of hyaluronic acid or hyaluronic acid derivative by reaction of the same, in the acid form or as a quaternary ammonium salt, with an activating agent, in acid solution or on acid resin wherein the activating agent is 1,1-carbonyldiimidazole;
b) reaction with an amine of an unsubstituted or substituted aliphatic, aromatic, arylaliphatic, cycloaliphatic, or heterocyclic series which is a 3- to 8-membered ring with at least one heteroatom selected from N, O and S.

20. The biomaterials according to claim 11, wherein the cross-linked collagen is cross-linked with aldehydes.

21. The biomaterial according to claim 9, further comprising at least one biologically active substance, wherein the biologically active substances are proteins and their fragments, peptides, polynucleotides, growth factors, enzymes, or vaccines.

22. Biomaterials according to claim 1 or claim 2, in association with fibrin, and optionally with other biologically active substances for the preparation of surgical glues, wherein the biologically active substances are proteins and their fragments, peptides, polynucleotides, growth factors, enzymes, or vaccines.

23. A scaffold for cell cultures comprising the biomaterials according to claim 1 or claim 2.

24. Surgical and health-care articles comprising the biomaterials according to claim 1 or claim 2.

25. Biomaterials according to claim 1 or claim 2, in the form of guide channels, gauzes, threads, gels, hydrogels, tampons, films, membranes, sponges, non-woven fabrics, microspheres, or nanospheres.

26. Surgical and health-care articles according to claim 24, in the form of guide channels, gauzes, threads, gels, hydrogels, tampons, films, membranes, sponges, non-woven fabrics, microspheres, or nanospheres.

27. The biomaterial according to claim 10, wherein the polysaccharide is selected from the group consisting of chitin, chitosan, pectin or pectic acid, agar, agarose, xanthane, gellan, alginic acid or alginates, polymannans or polyglycans, starch, and natural gums.

28. A pharmaceutical composition or biomaterial comprising a water-soluble amide compound of hyaluronic acid or a derivative thereof which comprises at least one repetitive unit of the following general formula:

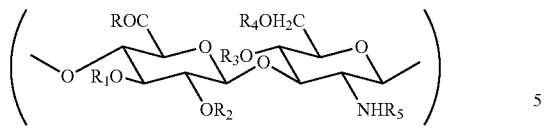

wherein:
R=NR$_6$R$_7$,
R$_1$, R$_2$, R$_3$, R$_4$=H;
R$_5$=CO—CH$_3$;
R$_6$=is H;
R$_7$=is a aliphatic, aromatic, arylaliphatic, cycloaliphatic, or heterocyclic group, substituted or unsubstituted;
with the proviso that R does not form an amide bond with a medicinal agent,
and wherein the percentage of amidation of the compound is up to about 5%,
and wherein said pharmaceutical composition comprises a pharmaceutically acceptable carrier.

* * * * *